United States Patent [19]

DiGuiseppi et al.

[11] Patent Number: 5,449,849
[45] Date of Patent: Sep. 12, 1995

[54] SELECTIVATED ZSM-035 CATALYST AND PROCESS FOR SELECTIVELY CONVERTING ETHENE TO LINEAR BUTENES THEREWITH

[75] Inventors: Frank T. DiGuiseppi, Yardville; Scott Han, Lawrenceville; Roland H. Heck, Pennington, all of N.J.

[73] Assignee: Mobil Oil Corporation, Fairfax, Va.

[21] Appl. No.: 228,770

[22] Filed: Apr. 18, 1994

[51] Int. Cl.[6] .......................... C07C 2/00; C07C 2/04
[52] U.S. Cl. ...................................... 585/510; 585/500
[58] Field of Search ................................ 585/510, 500

[56] References Cited

U.S. PATENT DOCUMENTS

| | | |
|---|---|---|
| 3,960,978 | 6/1976 | Givens et al. . |
| 4,002,697 | 1/1977 | Chen . |
| 4,021,502 | 5/1977 | Givens et al. . |
| 4,100,215 | 7/1978 | Chen . |
| 4,101,595 | 7/1978 | Chen et al. . |
| 4,423,269 | 12/1983 | Miller ................... 585/530 |
| 4,427,786 | 1/1984 | Miale et al. ............ 502/61 |
| 4,427,787 | 1/1984 | Miale et al. ............ 502/71 |
| 4,427,788 | 1/1984 | Miale et al. ............ 502/71 |
| 4,427,789 | 1/1984 | Miale et al. ............ 502/71 |
| 4,427,790 | 1/1984 | Miale et al. ............ 502/71 |
| 4,444,902 | 4/1984 | Chang et al. ........... 502/86 |
| 4,511,746 | 4/1985 | Miller .................... 585/570 |
| 4,520,221 | 5/1985 | Chen ..................... 585/517 |
| 4,568,786 | 2/1986 | Chen et al. ............ 585/517 |
| 4,605,805 | 8/1986 | Chang et al. .......... 585/510 |
| 4,607,130 | 8/1986 | Chang et al. .......... 585/510 |
| 4,678,766 | 1/1988 | Rosinski ................ 502/085 |
| 4,717,782 | 1/1988 | Garwood et al. ...... 585/531 |
| 4,870,038 | 9/1989 | Page et al. ............. 502/62 |
| 4,943,545 | 7/1990 | Chang et al. .......... 502/56 |
| 5,015,361 | 5/1991 | Anthes et al. ......... 208/111 |
| 5,284,989 | 2/1994 | Apelian ................. 585/533 |

FOREIGN PATENT DOCUMENTS 0089795  9/1983  European Pat. Off. .

Primary Examiner—Sharon A. Gibson
Assistant Examiner—E. D. Irzinski
Attorney, Agent, or Firm—Alexander J. McKillop; Dennis P. Santini; Laurence P. Hobbes

[57] ABSTRACT

The present invention relates to a catalyst and its use in a process for the conversion of ethene to a product rich in linear butenes, especially 2-butene, comprising contacting a feedstock comprising ethene under dimerization conditions with a catalyst composition comprising a porous crystalline silicate having the structure of ZSM-35 which has been treated by a) fluoriding, e.g., with $NH_4F$, and then b) at least partially surface deactivated for acid catalyzed reactions by chemisorption of a surface-deactivating agent which possesses an average cross section diameter greater than that of the zeolite pores, e.g., collidine.

6 Claims, No Drawings

SELECTIVATED ZSM-035 CATALYST AND PROCESS FOR SELECTIVELY CONVERTING ETHENE TO LINEAR BUTENES THEREWITH

BACKGROUND OF THE INVENTION

This invention relates to a process for the catalytic conversion of ethene to provide an oligomer product which is rich in linear butenes, especially 2-butene.

The process employs a selectivated ZSM-35 catalyst which exhibits unique characteristics under the process conditions described below.

Ethene is a by-product of petroleum refining and is, as well, a commodity petrochemical. Today much of the ethene generated during refining and some of the lower concentration ethene streams from petrochemical production are burned as fuel. Significant economic value could be derived if these ethene-containing streams could be processed to generate higher boiling, more valuable hydrocarbons from the ethene. Interest in making C4 olefins from ethene has increased in recent years as a way of utilizing ethene. 1-Buterie is a valuable petrochemical product while 2-butene is suited for use in alkylation processes to provide high octane gasoline components. In addition, since isomerization within the C4 olefin group is well-known, linear C4 olefin can be converted to isobutylene, an intermediate for t-butyl methyl ether (MTBE).

Conversion of olefins to gasoline and/or distillate products is disclosed in U.S. Pat. Nos. 3,960,978 and 4,021,502 (Givens, Plank and Rosinski) wherein gaseous olefins in the range of ethene to pentene, either alone or in admixture with paraffins are converted into an olefinic gasoline blending stock by contacting the olefins with a catalyst bed made up of a ZSM-5 type zeolite. Such a technique has been developed by Gatwood, et al, as disclosed in European Patent Application No. 83301391.5, published 29 Sept. 1983.

The prior art teaches conversion of $C_2+$ monoalkenes to an equilibrium olefin mixture under conditions which maximize the formation of higher olefins. For example, zeolites such as ZSM-5 are known to convert lower olefins to higher olefins. Conversion of lower olefins, especially propene and butenes, over HZSM-5 is effective at moderately elevated temperatures and pressures. Lower olefinic feedstocks containing $C_2$-$C_6$ alkenes may be converted selectively; however low severity conditions do not convert a major fraction of ethene. While propene, butene-1, and others may be converted to the extent of 50% to 95% at temperatures up to 400° C and moderate pressures from ambient to 5500 kPa, only about 10% to 30% of the ethene component will be converted using HZSM-5 or similar acid zeolites, according to U.S. Pat. No. 4,717,782 to Garwood et al. The olefin interconversion process must cope with undesirable side reactions which yield aromatics and paraffins, the presence of which is acutely noticed at the relatively high temperatures (>700° F.) at which ethene conversion and formation of i-$C_4$= and i-$C_5$= formation is thermodynamically favored. In order to avoid such undesirable side reactions, the '782 Garwood et al reference teaches the use of a bifunctional nickel-zeolite catalyst for oligomerizing ethene streams containing hydrogen and hydrogen sulfide at 100° to 450° C. and 200–3600 kPa (15–500 psig), wherein water is fed with the feedstock to prevent reduction of the nickel component.

Thus, it is of interest to find catalysts of increased activity which are able to convert ethene more selectively into butenes at higher feed rates, lower reaction pressures or with more dilute ethene streams and simultaneously minimize production of the higher oligomers.

Methods for enhancing the catalytic activity of zeolitic materials are known, including treatments involving fluorine. U.S. Pat. No. 4,444,902 relates to a process for enhancing acidic activity of a highly siliceous zeolite by contact with aluminum fluoride followed by ammonium exchange and calcination. U.S. Pat. No. 4,427,787 teaches zeolite activation by contacting an alumina-composited zeolite with hydrogen fluoride. Ammoniacal aluminum fluoride is taught as a reagent for zeolite activation in U.S. Pat. No. 4,427,788 while U.S. Pat. No. 4,427,789 teaches treatment of alumina-composited zeolite with alkali metal fluoride. U.S. Pat. No. 4,427,790 treats enhancing zeolite activity by treatment with a compound of the formula $L_{(n-m)}[MF_n]_3$ wherein L is an organic or inorganic ionic moiety, $[MF_n]$ is a fluoroanion moiety wherein M is a Group VB, VIB, VIIB, VIII, IIIA, IVA or VA element, n is the coordination number of M, m is the valence of M and 3 is the charge associated with L. U.S. Pat. No. 4,427,786 teaches the use of boron fluoride in activating an alumina- or gallia-supported zeolite. U.S. Pat. No. 4,678,766 utilizes an aqueous ammonium fluoride solution to enhance catalytic dewaxing selectivity of an oxygen calcined zeolite and reduce n-hexane cracking activity. U.S. Pat. No. 4,943,545 teaches activating zeolites which are framework aluminum-deficient but contain non-framework aluminum by contact with aqueous fluoride solution. Such fluoride solution can be prepared from a fluoride compound selected from the group consisting of ammonium fluoride ($NH_4F$), hydrofluoric acid (HF), and ammonium hydrogen fluoride ($NH_4F \cdot HF$).

It is also known in the art that surface acidity of zeolitic catalysts can be modified by treatment with various reagents. U.S. Pat. No. 4,870,038 to Page et al discloses a process for producing substantially linear hydrocarbons by oligomerizing a lower olefin at elevated temperature and pressure with siliceous acidic ZSM-23 whose surface is rendered substantially inactive for acidic reactions, e.g., by contact with 2,4,6-collidine (2,4,6-trimethylpyridine, gamma-collidine). U.S. Pat. No. 5,015,361 to Anthes et al discloses a method for catalytic dewaxing which employs surface acidity deactivated zeolite catalysts. The reduction in surface acidity serves to reduce the amount of lower value cracked products obtained during dewaxing. U.S. Pat. No. 4,101,595 teaches the modification of zeolites by exchange and similar technology with large cations such as $N+$ and $P+$ and large branched compounds such as polyamines and the like. Bulky phenolic and silicating zeolite surface-modifying agents are described in U.S. Pat. Nos. 4,100,215 and 4,002,697, respectively. As disclosed in U.S. Pat. Nos. 4,520,221 and 4,568,786, zeolites which have been surface-deactivated by treatment with bulky dialkylamines are useful as catalysts for the oligomerization of lower olefins such as propylene to provide lubricating oil stocks.

All of the foregoing references are incorporated herein by reference.

SUMMARY OF THE INVENTION

The present invention relates to a process for the conversion of ethene to a product rich in linear butenes comprising contacting a feedstock comprising ethene under dimerization conditions with a catalyst composition comprising a porous crystalline silicate having the structure of ZSM-35 zeolite. The ZSM-35 zeolite used in the conversion of ethene has been treated by a) fluoriding and then b) at least partially surface deactivated for acid catalyzed reactions by chemisorption of a surface-deactivating agent which possesses an average cross section diameter greater than that of the zeolite pores.

DETAILED DESCRIPTION OF PREFERRED EMBODIMENTS

Feed

The ethene feed to the dimerization reaction of the present invention can be a purified ethene stream or more commonly an impure ethene stream diluted with other hydrocarbons and other gases such as $H_2S$, $NH_3$, $N_2$, $H_2$, etc. Such diluent hydrocarbons can be, saturated hydrocarbons, such as ethane, propane, butane and the like and, unsaturated hydrocarbons, such as propene, butenes, pentenes and the like. The exact composition of the feed stream will depend upon its source. Generally, the feed can contain 10 to 90 wt % ethene, preferably 30 to 70 wt % ethene, e.g., 35 wt % ethene and 65 wt % nitrogen or air diluent. In one embodiment, the feedstock comprises unsaturated gas plant treated deethanizer overhead.

Catalyst

The catalyst composition of the present invention comprises a ZSM-35 crystalline silicate molecular sieve, optionally composited in an inorganic oxide matrix. ZSM-35 has channels described by 10-membered rings of T (=Si or Al) or oxygen atoms, i.e., it is an intermediate pore zeolite, distinct from small pore 8-ring or large pore 12-ring zeolites. It differs, however, from other intermediate pore 10-ring zeolites, such as ZSM-5, ZSM-11, ZSM-57 or stilbite, in having a smaller 10-ring channel.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D. An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974).

When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g., at 500° C. in air. Acid treatment may result in dealumination and is therefore not typically practiced. Other cations, e.g. metal cations, can be introduced by conventional base exchange or impregnation techniques.

The zeolite may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant processes. The relative proportions of finely divided zeolite and inorganic oxide gel matrix vary widely with the zeolite content ranging from about 1 to about 90 percent by weight and more usually in the range of about 30 to about 80 percent by weight of the composite. In other words, the catalyst composition can comprise 10 to 99 wt % of a refractory inorganic oxide binder, preferably 20 to 70 wt % of a silica binder.

Selectivation

A. Fluoriding

The fluoriding of the zeolite can be carried out by contacting said zeolite with a fluorine compound under conditions sufficient to provide a zeolite having a fluoride concentration of the equivalent of between 0.1 and 10 wt % fluorine, preferably between 0.1 and 5.0 wt % fluorine, e.g., between 0.5 and 2.0 wt % fluorine.

The fluorine compound employed in the fluoriding step of the present invention can be any suitable fluoride material for this purpose. Fluoriding methods for enhancing the catalytic activity of zeolitic materials are known, including treatments involving fluorine. U.S. Pat. No. 4,444,902 relates to a process for enhancing acidic activity of a highly siliceous zeolite by contact with aluminum fluoride followed by ammonium exchange and calcination. U.S. Pat. No. 4,427,787 teaches zeolite activation by contacting an alumina-composited zeolite with hydrogen fluoride. Ammoniacal aluminum fluoride is taught as a reagent for zeolite activation in U.S. Pat. No. 4,427,788 while U.S. Pat. No. 4,427,789 teaches treatment of alumina-composited zeolite with alkali metal fluoride. U.S. Pat. No. 4,427,790 treats enhancing zeolite activity by treatment with a compound of the formula $L_{(n-m)}[MF_n]_e$ wherein L is an organic or inorganic ionic moiety, $[MF_n]$ is a fluoroanion moiety wherein M is a Group VB, VIB, VIIB, VIII, IIIA, IVA or VA element, n is the coordination number of M, m is the valence of M and 3 is the charge associated with L. U.S. Pat. No. 4,427,786 teaches the use of boron fluoride in activating an alumina- or gallia-supported zeolite. U.S. Pat. No. 4,678,766 utilizes an aqueous ammonium fluoride solution to enhance catalytic dewaxing selectivity of an oxygen calcined zeolite and reduce n-hexane cracking activity. U.S. Pat. No. 4,943,545 teaches activating zeolites which are framework aluminum-deficient but contain non-framework aluminum by contact with aqueous fluoride solution. Such fluoride solution can be prepared from a fluoride compound selected from the group consisting of ammonium fluoride ($NH_4F$), hydrofluoric acid (HF), and ammonium hydrogen fluoride ($NH_4F \cdot HF$). All of these techniques are suitable for use in the fluoriding step of the present invention and the foregoing U.S. Patents are incorporated herein by reference, especially with respect to the fluoriding techniques disclosed therein.

In one embodiment, the fluoriding is carried out by contacting the catalyst composition (zeolite alone or zeolite and composite) with aqueous fluoride solution. The fluoride solution can be from 0,001 to 10 N, preferably about 0.01 to 0.1 N (equivalents of fluoride ion/liter). Contacting occurs under mild conditions such as a temperature of about 20° to 100° C., preferably 60° to 95° C. for about 0.1 to 48 hours, preferably 6 to 18 hours. The zeolite is contacted with the fluoride solution under conditions sufficient to provide a zeolite having a fluoride concentration of the equivalent of between 0.1 and 10 wt % fluorine, preferably between 0.3 and 3.0 wt % fluorine, say between 0.5 and 1.5 wt % fluorine.

The fluoride solution contacted catalyst composition may then be contacted with an aqueous ammonium ion solution of from 0.05 N to 5 N, preferably 0.5 to 2.0 N, at a temperature of from 20° to 100° C., preferably about 25° C., for a period sufficient to effect ammonium exchange, say 0.25 to 6 hours, preferably 0.5 to 3 hours. The aqueous ammonium ion solution contacted catalyst composition may then be calcined at a temperature of from 200° to 600° C., preferably about 500° to 550° C., for about 1 minute to 48 hours, preferably 0.5 to 6 hours, in order to convert the zeolite to the hydrogen form.

Preferably, the aqueous fluoride solution employed in the present invention can be prepared from a fluoride compound selected from the group consisting of ammonium fluoride ($NH_4F$), hydrofluoric acid (HF), and ammonium hydrogen fluoride ($NH_4F \cdot HF$). The fluoride solution employed can have an acidic character. The initial pH thereof may range from 0.1 to 6, preferably 2 to 4, whereas by the end of the fluoride contacting step it may increase to a pH between 2 and 8, preferably between 4 and 7.

B. Surface Deactivation

The extent to which the fluorided zeolite can be surface-deactivated can vary over considerable limits, depending on the conditions of the deactivation procedure, and still provide significant improvement over the same zeolite which has not been surface-deactivated. In general, a reduction in surface acid sites on the order of at least about 10%, and preferably at least about 20%, can be readily achieved employing the methods described below.

Deactivation of the surface acid catalytic activity of the selected zeolite can be accomplished in accordance with known and conventional methods. Thus, treatment of the zeolite surface with bulky basic compounds such as amines, phosphines, phenols, polynuclear hydrocarbons, cationic dyes, and the like, will provide the requisite reduction in surface acid catalytic activity.

These surface deactivating agents should have an average cross section diameter of about 5 Angstroms or greater in order to prevent their being sorbed within the zeolite. Examples of suitable amines include monoamines, diamines, triamines, aliphatic and aromatic cyclic amines and heterocyclic amines, porphines, phthalocyanines, 1,10-phenanthroline, 4,7-diphenyl-1,10-phenanthroline, 3,4,7,8-tetramethyl-1,10-phenanthroline, 5,6-benzoquinoline, 2,2':6',2"-terpyridine, 2,4,6-tris(2-pyridyl)-S-triazine and 2,3-cyclododecenopyridine. Examples of phosphines include triphenylphosphine and 1,2-bis(diphenylphosphine)ethane. Suitable phenols are, for example, di-t-butylphenol, alkylated naphthol and 2,4,6-trimethylphenol. Polynuclear hydrocarbons include substances such as pyrene and phenanthrene. Cationic dyes include thionine, methylene blue and triphenylmethane dyes, such as malachite green and crystal violet. Another surface modification technique is deactivation by treating with metal compounds. Suitable metal compounds are magnesium acetate, metal-porphines such as hemin or iron (III) porphine chloride, cobalticinium chloride ($(C_5H_5)_2COCl$) and titanocene dichloride (biscyclopentadienyl titanium dichloride) and large complex cations such as $[Co(NH_2R)_6]^{2+}$ where R is H or alkyl, $[Pt(NH_2R)_4]_{2+}$ where R is alkyl, $[Co(en)_3]^{3+}$ where en is ethylenediamine and manganese (III) meso-tetraphenylporphine.

The zeolites can also be treated with organic silicon compounds as described in U.S. Pat. Nos. 4,100,215 and 4,002,697, the contents of which are incorporated by reference herein, to impart the desired degree of surface deactivation while being essentially free of carbonaceous deposits. Such treatment involves contacting the catalyst with a silane surface-modifying agent capable of deactivating catalytic (acidic) sites located on the external surface of the zeolite by chemisorption.

Amines having an average cross section diameter larger than about 5 Angstroms are especially suitable for reducing zeolite surface acid catalysis activity. Examples of such amines include substituted quinolines, heterocyclic amines and alkyl-substituted pyridines such as 2,4 or 1,6-dialkyl pyridines and 2,4,6-trialkyl pyridines. Preferred are bulky, sterically-hindered di-ortho-alkyl pyridines such as 2,6-di-tert-butylpyridine as described in U.S. Pat. Nos. 4,520,221 and 4,568,786 referred to above, and 2,4,6-collidine (2,4,6-trimethyl pyridine, gamma-collidine) as disclosed in U.S. Pat. No. 4,870,038, the contents of which are incorporated herein by reference.

The zeolites used in the present invention can be contacted with the surface deactivating agent by adding small amounts of said agent to the feedstock which is to be subjected to dimerization conditions. Suitable amounts of surface deactivating agent in the feed can range from 0 01 to 10 wt %, preferably 0.5 to 5 wt %, say, 1 to 3 wt % of the feedstock. This concentration of deactivating agent in the feed is maintained until the cumulative moles of amine fed per mole of acid ($H^+$) in the zeolite reaches 0.2 to 0.5. Thereafter the concentration of deactivating agent in the feed is decreased to a maintenance level of 10 to 1000 ppm. The required maintenance level concentration will vary with the amine used and the conditions employed. This level can be adjusted to maintain the desired level of oligomers in the reactor product.

Alternatively, the zeolite can be treated with the agent prior to contact with the organic feedstock. Such treatment can be accomplished by contacting the zeolite with 0.0001 to 1.0 parts by weight, preferably 0.0005 to 0.5 parts by weight, say 0.001 to 0.05 parts by weight of the surface deactivating agent, per weight of zeolite, preferably dissolved in a solvent, e.g. pentane.

The regeneration of spent zeolite catalyst used in the dimerization reaction is carried out oxidatively or hydrogenatively employing procedures known in the art.

Ethene Conversion Conditions

The ethene conversion process of the present invention can be carried out by contacting the feedstock with the catalyst composition under conditions comprising temperatures ranging from said dimerization conditions comprise a temperature ranging from 150° C. to 400° C., preferably from 250° C. to 370° C., total unit inlet pressures ranging from 2 to 15 atm, preferably ranging from 5 to 8 atm, WHSV ranging from 0.1 to 5, preferably ranging from 0.5 to 2.0, and wherein at least 1%, preferably 2%, say 3% by weight of said ethene is converted. The resulting ethene conversion is carried out with an overall linear $C_4$ olefins selectivity of at least 50 wt %, preferably at least 65 wt % and a linear butenes to isobutylene molar ratio of at least 10, preferably at least 50. The ethene is converted with a selectivity of 2-butenes to 1-butene molar ratio of at least 2, preferably at least 3.

The reaction is desirably carried out in a fixed bed reactor although an ebullated, slurry or fluidized bed or other type of reactor can be useful.

The following examples provide specific illustrations for the present invention.

EXAMPLE 1

Preparation of ZSM-35

ZSM-35 was prepared according to the following mole ratios: $SiO_2/Al_2O_3 = 21.5$, $OH^-/SiO_2 = 0.11$, $H_2O/SiO_2 = 13.2$, $N/Al_2O_3 = 6.5OH^-/H_2O = 0.008$ The reagents used were 50% NaOH, $Al_2(SO_4)_3 \cdot 18\text{-}H_2O$, HiSil® silica available from PPG Industries, Chemical Division (USA), and pyrrolidine. After measuring out appropriate quantities, the reagents were introduced in the following order: $H_2O$, NaOH, aluminum sulfate, silica, and pyrrolidine. 0.2 wt. % ZSM-35 was added as seed crystals. The reaction mixture was heated to 100° C. and held at temperature with agitation for 106 hrs. The product was cooled, filtered, and washed with water. Conversion to the acid form involved calcination in air at 538° C., ammonium exchange using aqueous ammonium nitrate, washing with water, and nitrogen calcination at 538° C.

EXAMPLE 2

Fluoride Treatment of ZSM-35

The ZSM-35 catalyst composition of Example 1 was bulk exchanged with $NH_4F$ to give a 1% $F^-$ content in the catalyst as follows: The catalyst from Example 1 was wetted with aqueous $NH_4F$, containing the desired quantity of fluoride, and the solution evaporated off in vacuum. The catalyst was then calcined at 538° C. in nitrogen for four hours.

EXAMPLE 3

Surface Deactivation With Collidine of Fluoride Treated ZSM-35

The ZSM-35 catalyst composition of Example 2 was treated with the bulky base collidine (2,4,6 trimethylpyridine) to neutralize surface acidity by adsorption. 1 part of 2,4,6-collidine was dissolved in a minimum amount of pentane required to wet the catalyst and added to 99 parts of the base catalyst from Example 2. The mixture was stirred and the pentane allowed to evaporate. The finished catalyst was used without further treatment.

EXAMPLE 4

Surface Deactivation of Untreated ZSM-35

The catalyst from Example 1 was treated with the bulky base 2,4,6-collidine (2,4,6 trimethylpyridine) in the following manner. 1 part of 2,4,6-collidine was dissolved in a minimum amount of pentane required to wet the catalyst and added to 99 parts of the base catalyst from Example 1. The mixture was stirred and the pentane allowed to evaporate. The finished catalyst was used without further treatment.

EXAMPLE 5

Ethylene Conversion Over ZSM-35 Catalyst Compositions

A 65/35 (wt) stream of nitrogen/ethylene at 100 psig, 250 to 360° C. and 0.3 to 2.0 WHSV was converted over the catalyst compositions of Examples 1 to 4. The microreactor was of ⅜" o.d. containing 2.0 g of 20–40 meshed catalyst. After reaching desired conditions, product effluents were analyzed by gas chromatography (GC). The results set out in the Table below clearly show that fluoride and collidine-modified ZSM-35 of the present invention is more selective to linear butenes than the other catalysts tested. The 2-butenes constitute greater than 75% of n-butenes obtained with fluorided and collidine-modified ZSM-35 catalyst. Undesired C6+ products are also reduced.

TABLE

Dimerization of Ethylene
Base Catalyst - ZSM-35
Feed - 65/35 (wt) Nitrogen/Ethylene
Press - 100 PSIG

| | COLLIDINE | | | NONE | | | FLUORIDE AND COLLIDINE | | |
|---|---|---|---|---|---|---|---|---|---|
| Catalyst Pretreatment | | | | | | | | | |
| Temp, °C. | 250 | 300 | 325 | 230 | 250 | 265 | 360 | 360 | 360 |
| WHSV | 0.5 | 0.5 | 1.0 | 0.5 | 0.5 | 0.5 | 0.5 | 0.3 | 2.0 |
| Ethylene Conversion | 0 | 31 | 30 | 7 | 14 | 31 | 13 | 6 | 1 |
| Product Distribution, wt. % | | | | | | | | | |
| $C_3$'s | 0 | 3.0 | 2.3 | 0 | 0 | 0.3 | 9.8 | 13.5 | 9.6 |
| Isobutene | 0 | 22.0 | 18.1 | 8.1 | 13.0 | 9.5 | 1.9 | 0 | 0 |
| n-Butene | 0 | 22.8 | 17.8 | 14.9 | 13.0 | 8.2 | 66.4 | 78.2 | 69.9 |

TABLE-continued

Dimerization of Ethylene
Base Catalyst - ZSM-35
Feed - 65/35 (wt) Nitrogen/Ethylene
Press - 100 PSIG

| | COLLIDINE | | | NONE | | FLUORIDE AND COLLIDINE | | |
|---|---|---|---|---|---|---|---|---|
| Isobutane | 0 | 0.0 | 0.0 | 0.0 | 0.0 | 0.7 | 0 | 0 | 0 |
| N-Butane | 0 | 51.1 | 0.5 | 0.0 | 0.0 | 0.3 | 0.7 | 0 | 0 |
| $C_6+$ | 0 | 51.1 | 61.3 | 77.0 | 74.0 | 81.0 | 21.2 | 8.3 | 20.5 |
| Total | 0 | 100.0 | 100.0 | 100.0 | 100.0 | 100.0 | 100.0 | 100.0 | 100.0 |

Having thus clearly and objectively stated the problem to be solved, and its solution by the invention disclosed herein, and having provided a detailed description and illustrations of the best mode of practicing the invention, it is to be understood that no undue restrictions are to be imposed by reason thereof, and particularly, that the invention is not restricted to a slavish adherence to the details set forth herein.

What is claimed is:

1. A process for the conversion of ethene to a product comprising linear butenes comprising contacting a feedstock comprising ethene under dimerization conditions with a catalyst composition comprising a ZSM-35 zeolite which further comprises treating said catalyst composition prior to said contacting by a) fluoriding and then b) at least partially surface deactivating said catalyst composition for acid catalyzed reactions by chemisorption of a surface-deactivating agent which possesses an average cross section diameter greater than that of the zeolite pores.

2. The process of claim 1 which further comprises adding said surface-deactivating agent to said feedstock.

3. The process of claim 1 wherein said feedstock contains ethene in amounts greater than 50 wt % of total olefin content of said feedstock, said dimerization conditions comprise a temperature ranging from 150° C. to 400° C., total pressure ranging from 2 to 15 atm, weight hourly space velocity ranging from 0.1 to 5, and further comprising converting at least 1% by weight of said ethene with an overall linear $C_4$ olefins selectivity of at least 50 wt %, and a linear butenes to isobutylene molar ratio of at least 10.

4. The process of claim 3 wherein said temperature ranges from 250° C. to 370° C., said pressure ranges from 5 to 8 atm, said weight hourly space velocity ranges from 0.5 to 2.0, and further comprising converting at least 5% by weight of said ethene with an overall linear $C_4$ olefins selectivity of at least 65 wt %, and a linear butenes to isobutylene molar ratio of at least 50.

5. The process of claim 4 wherein said converting of ethene is carried out with a selectivity of 2-butenes to 1-butene molar ratio of at least 2.

6. The process of claim 5 wherein said converting of ethene is carried out with a selectivity of 2-butenes to 1-butene molar ratio of at least 3.

* * * * *